(12) United States Patent
Gries et al.

(10) Patent No.: US 9,789,044 B2
(45) Date of Patent: *Oct. 17, 2017

(54) COMPOUNDS AND METHODS FOR REPELLING BLOOD-FEEDING ARTHROPODS AND DETERRING THEIR LANDING AND FEEDING

(75) Inventors: Regine M. Gries, Coquitlam (CA); Grigori Khaskin, Coquitlam (CA); Gerhard G. Gries, Coquitlam (CA)

(73) Assignee: SCOTTS CANADA LTD, Toronto, Ontario (CA)

( * ) Notice: Subject to any disclaimer, the term of this patent is extended or adjusted under 35 U.S.C. 154(b) by 150 days.

This patent is subject to a terminal disclaimer.

(21) Appl. No.: 13/120,543

(22) PCT Filed: Sep. 25, 2009

(86) PCT No.: PCT/CA2009/001371
§ 371 (c)(1),
(2), (4) Date: Jun. 29, 2011

(87) PCT Pub. No.: WO2010/034127
PCT Pub. Date: Apr. 1, 2010

(65) Prior Publication Data
US 2011/0251270 A1    Oct. 13, 2011

Related U.S. Application Data

(60) Provisional application No. 61/100,556, filed on Sep. 26, 2008.

(51) Int. Cl.
*A01N 43/16* (2006.01)
*A01N 35/02* (2006.01)
(Continued)

(52) U.S. Cl.
CPC .............. *A61K 8/46* (2013.01); *A01N 31/02* (2013.01); *A01N 37/18* (2013.01); *A61Q 17/02* (2013.01)

(58) Field of Classification Search
None
See application file for complete search history.

(56) References Cited

U.S. PATENT DOCUMENTS 2,863,799 A   12/1958   Goodhue
3,034,950 A    5/1962   Goodhue
(Continued)

OTHER PUBLICATIONS

Roelofs, W.L., Sex Pheromone Perception: Synergists and Inhibitors for the Red-Banded Leaf Roller Attractant, J. Insect Physiol., 1971, vol. 17, pp. 435-448.*

(Continued)

*Primary Examiner* — Kathrien Cruz
*Assistant Examiner* — Andrew Lee
(74) *Attorney, Agent, or Firm* — Ulmer & Berne LLP

(57) ABSTRACT

This invention relates to a group of compounds for repelling blood-feeding ectoparasitic arthropods, and a method of deterring their landing and feeding on animals including humans, by applying in one or more formulations compounds that incorporate one or more sulfide and one or more hydroxyl groups to the skin, clothing or environment of animals, including humans. A method of repelling and deterring landing and feeding by blood-feeding arthropods on an animal by applying in effective amount one or more compounds that incorporate alkyl sulfide and alcohol moieties, or alkyl sulfide and amide moieties, or alkyl sulfide and amide moieties to the skin, clothing or environment of an animal.

24 Claims, 3 Drawing Sheets

(51) Int. Cl.
  A61K 8/46    (2006.01)
  A01N 31/02   (2006.01)
  A01N 37/18   (2006.01)
  A61Q 17/02   (2006.01)

(56) References Cited

U.S. PATENT DOCUMENTS

| | | | |
|---|---|---|---|
| 4,299,840 A * | 11/1981 | Skinner et al. | 514/424 |
| 4,427,700 A | 1/1984 | Retnakaran | |
| 4,876,090 A | 10/1989 | Weisler | |
| 5,621,013 A | 4/1997 | Beldock | |
| 6,437,001 B1 | 8/2002 | Roe | |
| 6,800,662 B2 | 10/2004 | Roe | |
| 6,897,244 B2 | 5/2005 | Zhu et al. | |
| 7,288,573 B2 | 10/2007 | Roe | |
| 2006/0235071 A1 | 10/2006 | Cantrell | |
| 2009/0069407 A1 | 3/2009 | Gries | |

OTHER PUBLICATIONS

Zaspel, Another Blood Feeder? Experimental Feeding of a Fruit-Piercing Moth Species on Human Blood in the Primorye Territory of Far Eastern Russia (Lepidoptera: Noctuidae: Calpinae), J. Insect Behavior, 2007, 20, pp. 437-451.*

Buttiker, The proboscis of eye-frequenting and piercing Lepidoptera (Insecta), Zoomorphology, 1996, 116, pp. 77-83.*

Peterson et al., Insect Repellents—Past, Present and Future, Pesticide Outlook, The Royal Society of Chemistry, 2001, 12, pp. 154-158.*

Athanase Badolo, et al., "Evaluation of the sensitivity of Aedes aegypti and Anopheles gambiae complex mosquitoes to two insect repellents: DEET and KBR 3023", Tropical Medicine and Int'l Health, vol. 9, No. 3, pp. 330-334, Mar. 2004.

Donald R. Barnard, et al., "Laboratory Evaluation of Mosquito Repellents Against Aedes albopictus, Culex nigripalpus, and Ochlerotatus triseriatus (Diptera: Culicidae)", Journal of Medical Entomology, 41(4):726-730, 2004.

G. M. Bennett, et al., "The Formation of Large Ring Monosulphides from Halogenated Sulphides with Extended Carbon Chains", Published Jan. 2, 1938, pp. 1891-1897; http:/rsc.org.

Eric Block, et al., "Lipoxygenase Inhibitors from the Essential Oil of Garlic, Markovnikov Addition of the Allyldithio Radical to Olefins", J. Am. Chem. Soc. 1988, 110, 7813-7827.

C. L. Cantrell, et al., "Isolation and Identification of Mosquito Bite Deterrent Terpenoids from Leaves of American (Callicarpa americana) and Japanese (Callicarpa japonica) Beautyberry", J. Agric. Food Chem. 2005, 53, 5948-5953.

Scott P. Carroll, et al., "PMD, a Registered Botanical Mosquito Repellent with Deet-like Efficacy", Journal of the American Mosquito Control Assoc., 22(3):507-514, 2006.

John F. Carroll, et al., "Repellency of two terpenoid compounds isolated from Callicarpa americana (Lamiaceae) against Ixodes scapularis and Amblyomma americanum ticks", Exp Appl. Acarol (2007) 41:215-224.

Mark S. Fradin, et al., "Comparative Efficacy of Insect Repellents Against Mosquito Bites", N Engl J Med, vol. 347, No. 1—Jul. 4, 2002, pp. 13-18.

Robert F. Harwood, et al., "Entomology in Human and Animal Health", Seventh Edition, Macmillan Publishing Co. Inc., pp. 1-14, 1979.

Catherine A. Hill, et al., "Arthropod-borne diseases: vector control in the genomics era", Nature Reviews/Microbiology, vol. 3, Mar. 2005, pp. 262-268.

Shengkui Hu, et al., "Photochemical Reactions of Sulfide-Containing Alkyl Phenylglyoxylates", Tetrahedron, vol. 53, No. 21, pp. 7165-7180, 1997.

Jun Kawabata, et al., "8-Methylsulfinyloctyl Isothiocyanate as an Allelochemical Candidate from Rorippa sylvestris Besser", Agric. Biol. Chem., 53 (12), 3361-3362, 1989.

Marcel S. F. Lie Ken Jie, et al., "1H and 13C N. M.R. Studies on the Positional Isomers of Methyl Thialaurate and Methyl Thiastearate", J. Chem. Soc. Perkin Trans. 11 1989, pp. 2121-2125.

John S. Mackenzie, et al., "Emerging flaviviruses: the spread and resurgence of Japanese encephalitis, West Nile and dengue viruses", Nature medicine, vol. 10, No. 12, Dec. 2004, pp. S98-S109.

A. T. A. Mairuhu, et al., "Dengue: an arthropod-borne disease of global importance", Eur J Clin Microbiol Infect Dis (2004) 23: 425-433.

G N Malavige, et al., "Dengue viral infections", Pestgrad Med. J. 2004 80, 588-601 (Jun. 21, 2011, pp. 588-602, downloaded from pmj.bmj.com).

Helio Amante Miot, et al., "Comparative Study of the Topical Effectiveness of the Andiroba Oil (Carapa guianensis) and DEET 50% as Repellent for Aedes sp", Rev. Inst. Med. trop. S. Paulo, 46(5):253-256, Sep.-Oct. 2004, pp. 253-256.

T. V. Rajan, et al., "A double-blinded, placebo-controlled trial of garlic as a mosquito repellant: a preliminary study", Medical and Veterinary Entomology (2005) 19, 84-89.

Re-evaluation Decision Document, "Personal insect repellents containing DEET (N,N-diethyl-m-toluamide and related compounds)", Pest Management Regulatory Agency, Apr. 15, 2002, pp. 1-44.

Report on the WHO Informal Consultation on the evaluation and testing of insecticides, WHO Pesticides Evaluation Scheme, Oct. 7-11, 1996, pp. 1-69.

R. Michael Roe, et al., "Development of a Novel All Natural Tick and Insect Repellent, Bioud, as a DEET replacement and for use on Cotton Fabric", 2006 Beltwide Cotton Conferences, San Antonio, TX, Jan. 3-6, 2006, pp. 1006-1016.

J. K. Trigg, "Evaluation of a Eucalyptus-Based Repellent Against Anopheles SPP. In Tanzania", Journal of the American Mosquito Control Assoc. 12(2):243-246, 1996.

Paolo M. De A. Zanotto, et al., "Population dynamics of flaviviruses revealed by molecular phylogenies" Proc. Natl. Acad. Sci. USA, vol. 93, pp. 548-553, Jan. 1996.

L. J. Zwiebel, et al., "Olfactory regulation of mosquito-host interactions", Insect Biochemistry and Molecular Biology 34 (2004) 645-652, Mar. 18, 2004.

\* cited by examiner

COMPOUNDS AND METHODS FOR REPELLING BLOOD-FEEDING ARTHROPODS AND DETERRING THEIR LANDING AND FEEDING

CROSS-REFERENCE TO RELATED APPLICATIONS

This application is the National Stage of International Application No. PCT/CA2009/001371, filed on Sep. 25, 2009, which claims the benefit of U.S. Provisional Patent Application No. 61/100,556, filed on Sep. 26, 2008.

FIELD OF THE INVENTION

This invention relates to a group of compounds for repelling blood-feeding ectoparasitic arthropods, and a method of deterring their landing and feeding on animals including humans, by applying in one or more formulations compounds that incorporate one or more sulfide and one or more hydroxyl groups to the skin, clothing or environment of animals, including humans. The invention further relates to a group of repellent and deterrent compounds that incorporate one or more sulfides and one or more amides.

BACKGROUND OF THE INVENTION

Haematophagous insects and certain other blood-feeding arthropods are ubiquitous ectoparasites of animals, including humans. In so doing, blood-feeding ectoparasitic arthropods constitute a major source of annoyance to humans and other animals, and are vectors of many microbial diseases, as well as those caused by viruses and virus-like disease agents (Harwood and James 1979).

Blood-feeding arthropods that annoy man and animals through their biting and feeding activity, and often vector disease-causing pathogens, comprise members of numerous insect taxa, including, but not limited to: flies in the Families Culicidae, Tabanidae, Psychodidae, Simuliidae, Muscidae and Ceratopgonidae (Order Diptera), bugs in the Families Cimicidae and Reduviidae (Order Hemiptera), lice in the Orders Mallophaga and Anoplura, and fleas in the Order Siphonaptera, as well as non-insectan arthropods, particularly ticks and mites in the Order Acari (also known as Acarina).

An example of a significant annoyance to humans and a major vector of disease-causing pathogens is the yellow fever mosquito, *Aedes aegypti* (Diptera: Culicidae), an exceptionally resilient blood-feeding species that breeds in any small container of water (Malavige et al. 2004). Adults are highly domesticated, typically resting indoors in dwellings, thus optimizing their opportunity to feed and vector pathogens that cause diseases such as yellow fever and dengue fever (Mackenzie et al. 2004; Malavige et al. 2004; Hill et al. 2005). Annually, 7.2 million humans become infected with yellow fever, and >30,000 die from the disease. Moreover, 50-100 million humans are infected with dengue fever (500,000 with its hemmorhagic form), resulting in approximately 24,000 deaths annually (Zanotto et al. 1996; Mairuhu et al. 2004). Other species of *Aedes*, as well as mosquitoes in other genera, particularly *Anopheles* and *Culex*, are also significant annoyance agents and vectors of disease-causing pathogens.

The most effective protection against mosquitoes and other ectoparasitic arthropods, is to repel them from, or deter their landing and feeding on, potential hosts. Until recently, the most efficacious known "repellent" was N,N-diethyl-m-toluamide (DEET) (Fradin and Day 2002). There are concerns associated with N,N-diethyl-m-toluamide. It is a solvent for some plastics, paints, varnishes and synthetic fabrics (Trigg 1996; Badolo et al. 2004; Miot et al. 2004). When used alone it may attract rather than repel *A. aegypti*. Finally, products exceeding 30% N,N-diethyl-m-toluamide are not recommended for protection of children (Pest Management Regulatory Agency 2002). Thus, there is a strong need for alternatives to N,N-diethyl-m-toluamide.

Research has led to several alternative repellents and deterrents to date, some of them with efficacy equal to that of N,N-diethyl-m-toluamide (Barnard and Xue 2004). Many of these are natural compositions, and include essential oils from plants (cedar, rosemary, eucalyptus, andiroba, catnip, thyme, neem, clove, soybean) and grease or oils from animals. Active ingredients in some of these oils have been isolated and formulated in commercial products. OFF!® botanicals, for example, contain p-menthane-3,8-diol from lemon *eucalyptus, Eucalyptus maculata citriodon* (Beldock et al. 1997; Carroll and Loye 2006) as the active ingredient. Other new repellents for mosquitoes and other arthropods that are found in natural sources include: 2-undecanone (methyl nonyl ketone) from tomato plants (Roe 2002, 2004, 2007; Roe et al. 2006); tetrahydronootkatone (1,4,4a,5,6,7, 8,10-octahydro-6-isopropyl-4,4a-dimethyl-2(1H)-naphthalenone) and 1,10-dihydronootkatone (1,4,4a,5,6,7,8,10-octahydro-6-isopropenyl-4,4a-dimethyl-2(1H)-naphthalenone) from yellow cedar (Zhu et al. 2005); and callicarpenal (13,14,15,16-tetranor-3-cleroden-12-al) and intermedeol [(4S,5S,7R,10S)-eudesm-11-en-4-ol] from American beautyberry (Cantrell et al. 2005, 2006; Carroll et al. 2007).

Most recently, Gries et al. (2009) report analyses of odorants in garlic essential oil with the objectives to (i) understand the moiety(ies) of molecules that convey offensive smell and insect repellency and (ii) engineer odorless compounds with greater repellency than their natural counterparts. The invention by Gries et al. (2009) relates to compounds that incorporate one or more allyl sulfide, allyl disulfide, and/or allyl polysulfide moieties, and one or more hydroxyl groups, and are used to repel or deter landing and feeding of mosquitoes on humans. 8-Allylsulfanyloctan-1-ol was the key compound which by itself or in combination with an adjuvant was more effective than DEET in deterring biting by the mosquitoes *Anopheles gambiae, Culex quinquefasciatus*, and *Aedes aegypti*.

SUMMARY OF THE INVENTION

The invention is directed to a method of repelling and deterring landing and feeding by blood-feeding arthropods on an animal by applying in effective amount one or more compounds that incorporate alkyl sulfide and alcohol moieties, or alkyl sulfide and amide moieties, or allyl sulfide and amide moieties to the skin, clothing or environment of an animal.

Compounds that incorporate alkyl sulfide and alcohol moieties can be aliphatic primary, secondary or tertiary alcohols with alkylsulfide moiety.

Said blood-feeding arthropod repellent and deterrent compounds can be selected from the group including, but not limited to, the following: 8-methylsulfanyloctan-1-ol, 8-ethylsulfanyloctan-1-ol, 8-propylsulfanyloctan-1-ol, 8-butylsulfanyloctan-1-ol, 8-pentylsulfanyloctan-1-ol, (N,N)-diethyl-8-allylsulfanyl-octanamide.

Effective amounts of said compounds that incorporate alkyl sulfide and alcohol moieties, or alkyl sulfide and amide moieties, or allyl sulfide and amide moieties can be combined with one or more additional compounds applied in effective amount to improve the repellent and deterrent effect against landing and feeding by blood-feeding arthropods.

The blood-feeding arthropods can include, but are not limited to, ticks and mites in the Order Acari (also known as Acarina) and insects in the Orders Mallophaga, Anoplura, Siphonaptera, Hemiptera (Families Cimicidae and Reduviidae), and Diptera (Families Culicidae, Tabanidae, Psychodidae, Simuliidae, Muscidae and Ceratopogonidae).

The blood-feeding insects in the family Culicidae can include, but are not limited to, species in the genera *Aedes, Culex, Anopheles, Chagasia, Bironella, Culiseta, Ochlerotatus, Psorophora, Toxorhynchites, Mansonia*, and *Coquillettidia*. The insects can be *Aedes aegypti, Anopheles gambiae* and *Culex quinquefasciatus*.

The animal can be a mammal, bird, reptile or amphibian. The mammal can be a human. The environment of an animal may include, but not be limited to, bedding, furniture, dwellings and vehicles.

An effective amount of said blood-feeding arthropod repellent and deterrent compounds can range from 1 nanogram to 100 milligrams per square centimeter of skin, clothing or environmental substrate.

The blood-feeding arthropod repellent and deterrent compounds can be formulated in an effective amount with a carrier material for application to the skin, clothing or environment of an animal.

The invention is also directed to a composition for repelling and deterring landing and feeding by blood-feeding arthropods on an animal comprising an effective amount one or more compounds that incorporate alkyl sulfide and alcohol moieties, or alkyl sulfide and amide moieties, or allyl sulfide and amide moieties.

DETAILED DESCRIPTION OF THE INVENTION

The inventors' own research (Gries et al. 2009) has shown that 9-allylsulfanylnonan-1-ol, 8-allylsulfanyloctan-2-ol, and 8-allylsulfanyloctan-1-ol are repellent to mosquitoes.

In this application, the inventors disclose the discovery of a new set of compounds, including 8-methylsulfanyloctan-1-ol, 8-ethylsulfanyloctan-1-ol, 8-propylsulfanyloctan-1-ol, 8-butylsulfanyloctan-1-ol, 8-pentylsulfanyloctan-1-ol and (N,N)-diethyl-8-allylsulfanyl-octanamide that among other insects are deterrent to mosquitoes.

Figure 1:
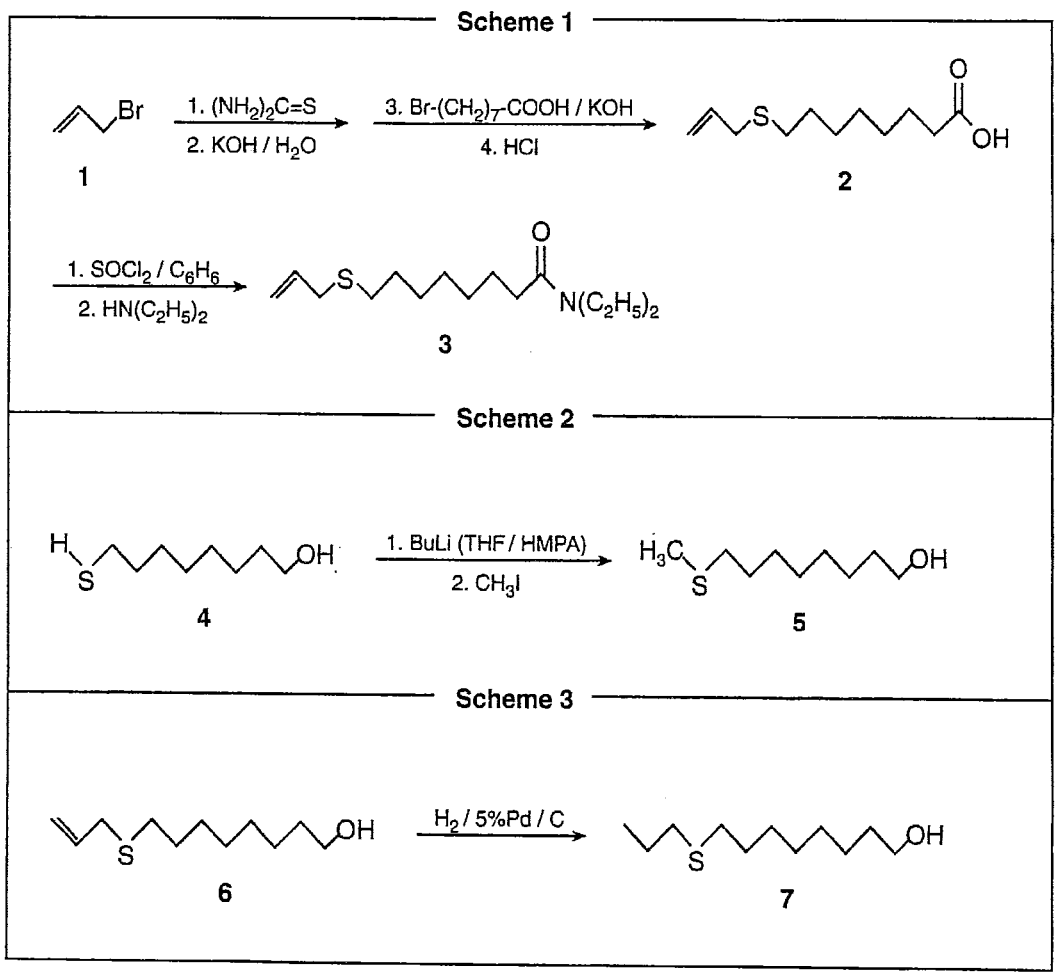
FIG. 1 illustrates synthetic pathways to (N,N)-diethyl-8-allylsulfanyl-octanamide (Scheme 1), 8-methylsulfanyl-1-octanol (Scheme 2), and 8-propylsufanyl-1-octanol (Scheme 3).

FIG. 1 illustrates synthetic pathways to (N,N)-diethyl-8-allylsulfanyl-octanamide (Scheme 1), 8-methylsulfanyl-1-octanol (Scheme 2), and 8-propylsufanyl-1-octanol (Scheme 3).

Example 1

Experimental Insects

A black-eyed Liverpool strain of *Aedes. aegypti* was obtained from Dr. Carl Lowenberger, Simon Fraser University (SFU). Insects were reared under standardized conditions (60-70% relative humidity, 26-28° C., 14 h light:10 h dark photoperiod) in SFU's insectary. Neonate larvae that hatched in glass dishes of sterilized hypoxic water were transferred to trays of distilled water provisioned with Nutrafin® Basix Staple Food fish diet. Pupae were collected daily and separated by sex, and 15 females and 10 males were placed in a paper cup (7.5 cm diameter, 8.5 cm high) with a mesh lid. Emergent adults were fed a 10% (w/v) sucrose solution via braided cotton dental rolls. Arm-fed gravid females were offered water-containing paper cups, lined with paper-towel as an oviposition substrate.

Example 2

General Bioassay Procedure

Candidate repellents and deterrents were bioassayed according to a modified protocol from the World Health Organization (1996). At least 1 hour prior to each bioassay, 75 host-seeking non blood-fed, nulliparous, 5- to 8-day-old female *Aedes aegypti* were placed into a wood-framed cage (26.5 cm on each side and 42.5 cm high) with a wooden floor, screened mesh sides and top, and a clear acrylic front fitted with a cotton stockinette sleeve (10 cm diameter). The test subject's arm was covered with an elbow-length polyethylene glove with an excised patch (16.6 cm long, 6 cm wide) to expose the ventral forearm of the test subject. Candidate deterrents were formulated in mineral (paraffin) oil and applied to the exposed forearm 5 min prior to inserting the arm into the cage. The inserted arm remained in the cage for 3 min every 30 min. Prior to each 3-min bioassay period, the hand of the untreated arm was inserted into the cage to ascertain that it received 10 bites within 30 sec as an indication of "biting pressure".

The bioassay was terminated when the treated arm received ≥2 bites in one 3-min bioassay period or one bite in each of two consecutive bioassay periods. The time elapsed from experiment initiation to first bite was recorded as deterrent failure or complete protection time.

Example 3

Synthesis of (N,N)-Diethyl-8-allylsulfanyl-octanamide (FIG. 1, Scheme 1)

A mixture of allylbromide (1, 1.30 ml, 15 mmol) and thiourea (1.45 g, 15 mmol) was refluxed in 50 ml of anhydrous ethanol for 3 hours and cooled to 25° C. Pellets of KOH (1.62 g, 30 mmol) were added together with water (0.30 ml). The reaction mixture was then refluxed for 2 hours. 8-Bromooctanoic acid was alkylated with potassium allylmercaptade (Jie et al. 1989) by adding to the reaction mixture 8-bromooctanoic acid (2.23 g, 10 mmol) and KOH (1.30 g), and refluxing for 5 hours under argon. Thereafter, water (50 ml) was added and the reaction mixture was extracted with hexane (2×40 ml). The aqueous solution was acidified with conc. HCl and extracted again with ether (2×40 ml). Ethereal extracts were washed with a saturated aq. NaCl solution and were dried over anh. $MgSO_4$. Evaporation of solvents gave 8-allylsulfanyl-octanoic acid (2) (50% pure by GC); MS [m/z (rel. intensity)]: 216 (M+,100), 199 (26); 169 (20), 157 (37), 139 (18), 123 (19), 113 (49), 95(26), 87 (34), 74 (69), 55 (52), 45(62), 41 (69).

Without further purification, the crude acid was dissolved in dry benzene (50 ml), and freshly distilled thionyl chloride (1.50 ml) was added. The reaction mixture was warmed to 50° C. and stirred for 5 hours under argon. Excess thionyl chloride and benzene were removed in vacuo. The residue in 20 ml of ether was stirred at 0° C., and diethylamide (4 ml) was added slowly. After 20 min, water (10 ml) was added and the product was extracted (2×40 ml) with a 1:1 ether/hexane mixture. Extracts were washed with a saturated aq. NaCl solution, dried over anh. $MgSO_4$, concentrated and purified by flash chromatography, using ether/hexane mixtures with increasing proportions of ether (40, 50 and 70%) as consecutive eluents. The yield of (N,N)-diethyl-8-allylsulfanyl-octanamide (3)(75% pure by GC) was 0.87 g (24% yield); MS [m/z (rel. intensity)]: 272 (M+1, 74), 230 (100), 198 (44), 157 (20), 126 (24), 115 (36), 100 (66), 74 (48), 58 (31), 44 (29).

Example 4

Synthesis of 8-methylsulfanyl-1-octanol (FIG. 1, Scheme 2)

A 2.5 M BuLi solution (4 ml, 10 mmol) in hexane was added at −78° C. under stirring to 8-mercapto-1-octanol (4) (0.84 g, 4.76 mmol) (Narchem Corp., Chicago Ill.) dissolved in a 4:1 mixture of THF/HMPA. After 30 min, iodomethane (0.6 ml, 10 mmol) was added in one portion. The reaction mixture was allowed to warm to room temperature, quenched with water, and extracted with ether (2×30 ml). Ethereal extracts were washed with a saturated aq. NaCl solution, dried over anh. $MgSO_4$, and concentrated. Purification by flash chromatography afforded 0.65 g of known 8-methylsulfanyl-1-octanol (5) (Bennett & Gudgeon 1938; Kawabato et al. 1989) (>99% pure by GC, 78% yield).

Other 8-alkylsulfanyl-1-octanols, including 8-methylsulfanyloctan-1-ol, 8-ethylsulfanyloctan-1-ol (compound previously known; Hu & Neckers, 1997), 8-propylsulfanyloctan-1-ol, 8-butylsulfanyloctan-1-ol and 8-pentylsulfanyloctan-1-ol were furnished in similar ways.

Example 5

Synthesis of 8-propylsulfanyl-1-octanol (FIG. 1, Scheme 3)

8-Propylsulfanyl-1-octanol (7) was produced via hydrogenation of 8-allylsulfanyl-1-octanol (6) (Gries et al. 2009) in hexanes with 5% Pd/C as a catalyst (quantitative yield).

Example 6

Deterrence of Five 8-alkylsulfanyloctan-1-ols Against *Aedes aegypti*

To determine the deterrence of 8-allylsulfanyloctan-1-ols against *Aedes aegypti*, a 10% formulation of either 8-methylsulfanyloctan-1-ol, 8-ethylsulfanyloctan-1-ol, 8-propylsulfanyloctan-1-ol, 8-butylsulfanyloctan-1-ol, or 8-pentylsulfanyloctan-1-ol in mineral oil was applied in Experiments 1-5 at a dose of 1.5 mg (total composition) per $cm^2$ to the skin of the test person, and was bioassayed according to the protocol described under EXAMPLE 2. In Experiment 6, a 10% formulation of 8-allylsulfanyl-1-octanol (Gries et al. 2009) in mineral oil was bioassayed for comparison. Each of Experiments 1-6 was replicated 3-4 times.

Figure 2:
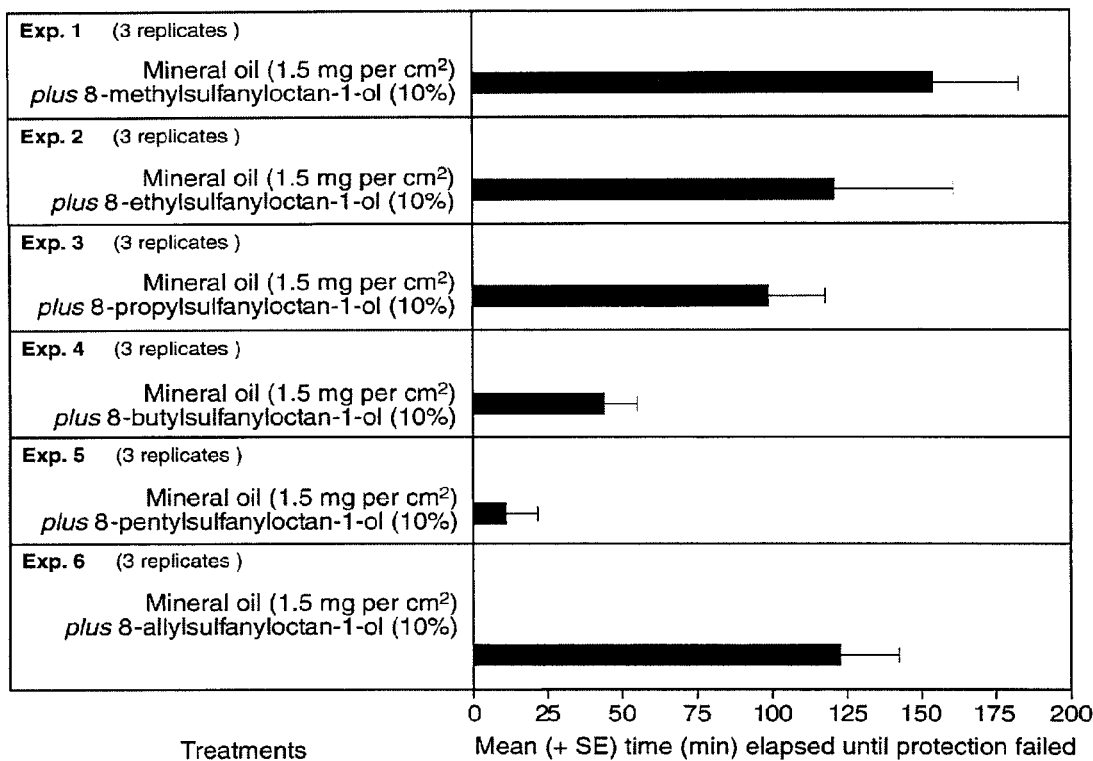
FIG. 2 shows the duration of protection of a 100 $cm^2$ area of an exposed human forearm from bites by *Aedes aegypti* caused by 10% formulations of either 8-methylsulfanyloctan-1-ol (experiment 1), 8-ethylsulfanyloctan-1-ol (experiment 2), 8-propylsulfanyloctan-1-ol (experiment 3), 8-butylsulfanyloctan-1-ol (experiment 4), 8-pentylsulfanyloctan-1-ol (experiment 5) or 8-allylsulfanyloctan-1-ol (experiment 6) in mineral oil applied to the skin at a dose of 1.5 mg per $cm^2$, as opposed to no protection provided by mineral oil alone.

In Experiments 1-5, 10% formulations of the 8-alkylsulfanyl-octan-1-ols in mineral oil provided protection from bites by *Aedes egypti* for an average duration ranging between 11-154 minutes (FIG. 2). The duration of protection was inversely related to the length of the alkyl chain. In Experiment 6, a 10% formulation of previously reported 8-allylsulfanyl-1-octanol provided protection for an average duration of 123 minutes.

FIG. 2 shows the duration of protection of a 100 $cm^2$ area of an exposed human forearm from bites by *Aedes aegypti* caused by 10% formulations of either 8-methylsulfanyloctan-1-ol (experiment 1), 8-ethylsulfanyloctan-1-ol (experiment 2), 8-propylsulfanyloctan-1-ol (experiment 3), 8-butylsulfanyloctan-1-ol (experiment 4), 8-pentylsulfanyloctan-1-ol (experiment 5) or 8-allylsulfanyloctan-1-ol (experiment 6) in mineral oil applied to the skin at a dose of 1.5 mg per $cm^2$, as opposed to no protection provided by mineral oil alone.

Example 7

Deterrence of (N,N)-diethyl-8-allylsulfanyl-octanamide against *Aedes aegypti*

To determine the deterrence of (N,N)-diethyl-8-allylsulfanyl-octanamide against *Aedes aegypti*, a 10% formulation of (N,N)-diethyl-8-allylsulfanyl-octanamide in mineral oil was applied in Experiment 7 at a dose of 1.5 mg (total composition) per $cm^2$ to the skin of the test person, and was bioassayed according to the protocol described under EXAMPLE 2. Experiment 7 was replicated 4 times.

In Experiment 7, a 10% formulation of (N,N)-diethyl-8-allylsulfanyl-octanamide in mineral oil provided protection from bites by *Aedes egypti* for an average duration of 156 min, which was slightly longer than the average duration of protection provided by 8-allylsulfanyl-1-octanol in Experiment 6.

Figure 3:
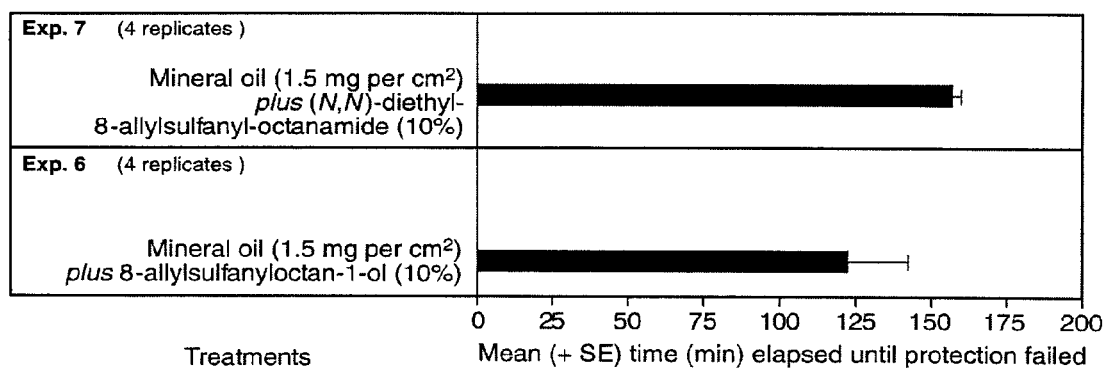
FIG. 3 shows the duration of protection of a 100 $cm^2$ area of an exposed human forearm from bites by *Aedes aegypti* caused by 10% formulations of (N,N)-diethyl-8-allylsulfanyl-octanamide (experiment 7) or 8-allylsulfanyloctan-1-ol (experiment 6) in mineral oil applied to the skin at a dose of 1.5 mg per $cm^2$, as opposed to no protection provided by mineral oil alone.

FIG. 3 shows the duration of protection of a 100 $cm^2$ area of an exposed human forearm from bites by *Aedes aegypti* caused by 10% formulations of (N,N)-diethyl-8-allylsulfanyl-octanamide (experiment 7) or 8-allylsulfanyloctan-1-ol (experiment 6) in mineral oil applied to the skin at a dose of 1.5 mg per $cm^2$, as opposed to no protection provided by mineral oil alone.

REFERENCES

U.S. Patent Documents

Beldock, D. T., Beldock, J. A., and Mudge, G. 1997. Insect repellent blends, lotions and sprays. U.S. Pat. No. 5,621, 013.

Cantrell, C. L., Klun, J. A., and Duke, S. O. 2006. Novel chlerodanes and methods for repelling arthropods. U.S. Patent Application Publication No. US 2006/0235071.

Gries, R. M., Gries, G. G., Khaskin, G., Avelino, N., and Campbell, C. 2009. Compounds, compositions and methods for repelling blood-feeding arthropods and deterring their landing and feeding. United States Patent Application Publication No. US 2009/0069407.

Roe, R. M. 2002. Method of repelling insects. U.S. Pat. No. 6,437,001.

Roe, R. M. 2004. Method of repelling insects. U.S. Pat. No. 6,800,662.

Roe, R. M. 2007. Method of repelling insects. U.S. Pat. No. 7,288,573.

Retnakaran, A. 1984. Repellent for black fly. U.S. Pat. No. 4,427,700.

Weisler, R. 1989. Systemic insect repellent composition and method. U.S. Pat. No. 4,876,090.

Zhu, B. C. R., Henderson, G., and Laine, R. A. 2005. Dihydronootkatone and tetrahydronootkatone as repellents to arthropods. U.S. Pat. No. 6,897,244.

PUBLICATIONS

Badolo, A., Ilboudo-Sanogo, E., Ouedraogo, A. P., and Costanti, C. 2004. Evaluation of the sensitivity of Aedes aegypti and Anopheles gambiae complex mosquitoes to two insect repellents: DEET and KBR 3023. Trop. Med. Int. Hlth. 9: 330-334.

Barnard, D. R. and Xue, R.-D. 2004. Laboratory evaluation of mosquito repellents against Aedes albopictus, Culex nigripalpus, and Ochlerotatus triseriatus (Diptera: Culicidae). J. Med. Entomol. 41: 726-730.

Bennett, G. M., and Gudgeon, H. 1938. The formation of large ring monosulphides from halogenated sulphides with extended carbon chains. J. Chem. Soc. 1891-1897.

Block, E., Rajeshwari, I., Grisoni, S., Saha, C., Belman, S., and Lossing, F. P. 1988. Lipoxygenase inhibitors from essential oil of garlic. Markovnikov addition of the allyldithio radical to olefins. J. Am. Chem. Soc. 110: 7813-7827.

Cantrell, C. L., Klun, J. A., Bryson, C. T., Kobaisy, M., and Duke, S. O. 2005. Isolation and identification of mosquito bite deterrent terpenoids from leaves of American (Callicarpa Americana) and Japanese (Callicarpa japonica) beautyberry. J. Agric. Food Chem. 53: 5948-5953.

Carroll, J. F., Cantrell, C. L., Klun, J. A., and Kramer, M. 2007. Repellency of two terpenoid compounds isolated from Callicarpa Americana (Lamiaceae) against Ixodes scapularis and Amblyomma americanum ticks. Exp. Appl. Acarol. 41: 215-224.

Carroll, S. P., and Loye, J. 2006. PMD, a registered botanical mosquito repellent with DEET-like efficacy. J. Am. Mosq. Cont. Assoc. 22: 707-514.

Fradin, M. S., and Day, J. F. 2002. Comparative efficacy of insect repellents against mosquito bites. N Engl. J. Med. 347: 13-18.

Harwood, R. F. and James, M. T. 1979. Entomology in human and animal health. 7$^{th}$ Ed. Macmillan, New York. 548 pp.

Hu, S. and Neckers, D. C. 1997. Photochemical reactions of sulfide-containing alkyl phenylglyoxylates. Tetrahedron 52: 7165-7180.

Hill, C. A., Kafatos, F. C., Stansfield, S. K., and Collins, F. H. 2005. Arthropod-borne diseases: vector control in the genomics era. Nature Rev. Microbiol. 3: 262-268.

Kawabato, J., Fukushi, Y., Hayashi, R., Suzuki, K., Mishima, Y., Yamato, A. and Mizutami, J. 1989. 8-Methylsufinyloctyl isothiosyanate as an allelochemical candidate from Rorippa sylvestris Besser. Agric. Biol. Chem. 53: 3361-3362.

Lie Ken Jie, M. S. F. and Bakare, O. 1989. $^1$H and $^{13}$C N.M.R. studies of the positional isomers of methyl thialaurate and methyl thiastearate. J. Chem. Soc. Perkin 2: 2121-2126.

Mackenzie, J. S., Gubler, D. J., and Petersen, L. R. 2004. Emerging flaviviruses: the spread and resurgence of Japanese encephalitis, West Nile and Dengue viruses. Nature Medicine 10: S98-S109.

Mairuhu, A. T. A., Wagenaar, J., Brandj es, D. P. M., and van Gorp, E. C. M. 2004. Dengue: and arthropod-borne disease of global importance. Eur. J. Clin. Microbiol. Infect. Dis. 23: 425-433.

Malavige, G. N., Fernando, S., Fernando, D. J., and Seneviratne, S. L. 2004. Dengue viral infections. Postgrad. Med. J. 80: 588-601.

Miot, H. A., Batistella, R. F., Batista, K. A., Volpato, D. E. C., Augusto, L. S. T., Madeira, N. G., Haddad Jr., V., and Miot, L. D. B. 2004. Comparative study of the topical effectiveness of the andiroba oil (Carapa guianensis) and DEET 50% as a repellent for Aedes sp. Rev. Inst. Med. Trop. S. Paulo. 46: 253-256.

Pest Management Regulatory Agency, Health Canada. 2002. Personal insect repellents containing DEET (N,N-diethyl-m-toluamide and related compounds). Re-evaluation Decision Document No. RRD2002-01. 41 pp.

Rajan, T. V., Hein, M., Porte, P., Wikel, S. 2005. A double-blinded, placebo-controlled trial of garlic as a mosquito repellant: a preliminary study. Med. Vet. Entomol. 19:84-89.

Roe, R. M., Donohue, K. V., and Jones, A. 2006. Development of a novel all natural tick and insect repellent, BIOUD, as a DEET replacement and for use on cotton fabric. Pp. 1006-1016. In: Proc. 2006 Beltwide Cotton Conf., San Antonio Tex.—Jan. 3-6, 2006.

Trigg, J. K. 1996. Evaluation of a eucalyptus-based repellent against Anopheles spp. in Tanzania. J Am. Mosq. Contr. Assoc. 12: 243-246.

World Health Organization. 1996. Report of the WHO informal consultation on the evaluation and testing of insecticides. CID/WHOPEWS/IC/96.1. p. 69.

Zanotto, P. M. D., Gould, E. A., Gao, G. F., Harvey, P. H., and Holmes, E. C. 1996. Population dynamics of flaviviruses revealed by molecular phylogenies. Proc. Nat. Acad. Sci. USA. 93: 548-553.

Zwiebel, L. J., and Takken, W. 2004. Olfactory regulation of mosquito-host interactions. Insect Biochem. Mol. Biol. 34: 645-652.

What is claimed is:

1. A method of repelling and deterring landing and feeding by blood feeding arthropods on an animal, comprising applying an effective amount of one or more compounds selected from the group consisting of 8-methylsulfanyloctan-1-ol, 8-ethylsulfanyloctan-1-ol, 8-propylsulfanyloctan-1-ol, 8-butylsulfanyloctan-1-ol, 8-pentylsulfanyloctan-1-ol, and (N,N)-diethyl-8-allylsulfanyl-octanamide, wherein the one or more compounds is for application to the skin, clothing or environment of the animal, and wherein the arthropods are blood feeding insects in the Order Diptera.

2. The method of claim 1, further comprising combining effective amounts of said one or more compounds with effective amounts of one or more additional compounds selected from the group consisting of: vanillin, 1,8-cineole, linalool, citronellal, citronellol, camphor, menthone, isomenthone, menthol, borneol, isomenthol, α-terpineol, cis- and trans-piperitol, nerol, neral, cinnamaldehyde, cumin aldehyde, geraniol, geranial, thymol, bornyl acetate, menthyl acetate, cumin alcohol, geranyl formate, geranyl acetate, caryophyllene, cis-cinnamyl acetate, N,N-diethyl-m-toluamide, p-menthane-3,8-diol, 2-undecanone, tetrahydronootkatone, 1,10-dihydronootkatone, callicarpenal, and intermedeol.

3. The method of claim 1, wherein the blood feeding insects in the Order Diptera comprises the Family Culicidae which comprise species in the genera *Aedes, Culex, Anopheles, Chagasia, Bironella, Culiseta, Ochlerotatus, Psorophora, Tocorhynchites, Mansonia* and *Coquilettidia*.

4. The method of claim 3, wherein the insects in the Family Culicidae are *Aedes aegypti, Anopheles gambiae*, and *Culex quinquefasciatus*.

5. The method of claim 1, wherein the animal is a mammal, bird, reptile or amphibian.

6. The method of claim 5, wherein the mammal is a human.

7. The method of claim 1, wherein the environment of the animal comprises the outdoors, bedding, furniture, dwellings and vehicles.

8. The method of claim 1, wherein an effective amount of said blood feeding arthropod repellent and deterrent compounds range from 1 nanogram to 100 milligrams per square centimeter of skin, clothing or an environmental substrate.

9. The method of claim 1, wherein said blood feeding arthropod repellent and deterrent compounds are formulated in effective amount with suitable inert ingredients to form a liquid, gel, paste, soap, spray, aerosol or powder.

10. A composition for repelling and deterring landing and feeding by blood feeding arthropods on an animal comprising an effective amount of one or more compounds selected from the group consisting of 8-methylsulfanyloctan-1-ol, 8-ethylsulfanyloctan-1-ol, 8-propylsulfanyloctan-1-ol, 8-butylsulfanyloctan-1-ol, 8-pentylsulfanyloctan-1-ol, and (N,N)-diethyl-8-allylsulfanyl-octanamide, and a suitable carrier, wherein the composition is for application to the skin, clothing or environment of the animal, and wherein the arthropods are blood feeding insects in the Order Diptera.

11. The composition of claim 10, further comprising effective amounts of one or more additional compounds selected from the group consisting of: vanillin, 1,8-cineole, linalool, citronellal, citronellol, camphor, menthone, isomenthone, menthol, borneol, isomenthol, α-terpineol, cis- and trans-piperitol, nerol, neral, cinnamaldehyde, cumin aldehyde, geraniol, geranial, thymol, bornyl acetate, menthyl acetate, cumin alcohol, geranyl formate, geranyl acetate, caryophyllene, cis-cinnamyl acetate, N,N-diethyl-m-toluamide, p-menthane-3,8-diol, 2-undecanone, tetrahydronootkatone, 1,10-dihydronootkatone, callicarpenal, and intermedeol.

12. The composition of claim 10, wherein the blood feeding insects in the Order Diptera comprises the Family Culicidae which comprise species in the genera *Aedes, Culex, Anopheles, Chagasia, Bironella, Culiseta, Ochlerotatus, Psorophora, Tocorhynchites, Mansonia* and *Coquilettidia*.

13. The composition of claim 12, wherein the insects in the Family Culicidae are *Aedes aegypti, Anopheles gambiae*, and *Culex quinquefasciatus*.

14. The composition of claim 10, wherein the animal is a mammal, bird, reptile or amphibian.

15. The composition of claim 10, wherein the mammal is a human.

16. The composition of claim 10, wherein the environment of the animal comprises the outdoors, bedding, furniture, dwellings and vehicles.

17. The composition of claim 10, wherein effective amounts of said blood feeding arthropod repellent and deterrent compounds range from 1 nanogram to 100 milligrams per square centimeter of skin, clothing or an environmental substrate.

18. The composition of claim 10, wherein said blood feeding arthropod repellent and deterrent compounds are formulated in effective amount with suitable inert ingredients to form a liquid, gel, paste, soap, spray, aerosol or powder for application to the skin, clothing or environment of an animal.

19. A method of repelling blood feeding insects of the Order Diptera from an animal, comprising applying an effective amount of one or more compounds of 8-methylsulfanyloctan-1-ol, 8-ethylsulfanyloctan-1-ol, 8-propylsulfanyloctan-1-ol, 8-butylsulfanyloctan-1-ol, 8-pentylsulfanyloctan-1-ol, or (N,N)-diethyl-8-allylsulfanyl-octanamide, to the skin, clothing or environment of the animal.

20. The method of claim 19, wherein the blood feeding insects of the Order Diptera is a member of the family of Culcidae, Tabanidae, Pychodidae, Simuliidae, Muscidae, or Ceratopogonidae.

21. The method of claim 20, wherein the member of the family of Culcidae is a member of the genera *Aedes, Culex, Anopheles, Chagasia, Bironella, Culiseta, Ochlerotaqtus, Psorophora, Toxorhynchites, Mansonia*, or *Coquillettidia*.

22. The method of claim 21, wherein the member of the family of Culcidae is *Aedes aegypti, Anopheles gambiae*, or *Culex quinquefasciatus*.

23. The method of claim 19, wherein the mammal is a human.

24. The method of claim 19, wherein the effective amount of the one or more compounds is from 1 nanogram per square centimeter of skin, clothing or environment of the animal to 100 milligrams per square centimeter of skin, clothing or environment of the animal.

* * * * *